US009121002B2

(12) United States Patent
Mano et al.

(10) Patent No.: US 9,121,002 B2
(45) Date of Patent: Sep. 1, 2015

(54) ENZYMATIC MODIFICATIONS OF A CELLULAR MONOLITHIC CARBON AND USES THEREOF

(75) Inventors: Nicolas Mano, Talence (FR); Victoria Flexer, Bordeaux (FR); Nicolas Brun, Bordeaux (FR); Rénal Backov, Bordeaux-Cauderan (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 13/521,835

(22) PCT Filed: Jan. 19, 2011

(86) PCT No.: PCT/FR2011/050093
§ 371 (c)(1),
(2), (4) Date: Jul. 12, 2012

(87) PCT Pub. No.: WO2011/089356
PCT Pub. Date: Jul. 28, 2011

(65) Prior Publication Data
US 2013/0101905 A1    Apr. 25, 2013

(30) Foreign Application Priority Data
Jan. 20, 2010   (FR) ..................................... 10 50361

(51) Int. Cl.
*C12M 1/00*    (2006.01)
*C04B 35/52*    (2006.01)
(Continued)

(52) U.S. Cl.
CPC ................. *C12M 23/00* (2013.01); *B05D 5/00* (2013.01); *C04B 35/521* (2013.01); *C04B 38/0032* (2013.01); *C12Q 1/26* (2013.01); *H01M 4/8605* (2013.01); *H01M 4/90* (2013.01);
(Continued)

(58) Field of Classification Search
None
See application file for complete search history.

(56) References Cited

U.S. PATENT DOCUMENTS 5,272,087 A * 12/1993 El Murr et al. .......... 204/403.04
5,376,251 A    12/1994 Kaneko et al.
(Continued)

FOREIGN PATENT DOCUMENTS

FR         2937970       5/2010
WO       2010049650      5/2010

OTHER PUBLICATIONS

Designing carbonaceous foams electrodes for efficient enzymatic biofuel cells.
(Continued)

*Primary Examiner* — Patrick Ryan
*Assistant Examiner* — Haixia Zhang
(74) *Attorney, Agent, or Firm* — Sofer & Haroun, LLP

(57) ABSTRACT

A porous electrochemical electrode is made up of a solid cellular material provided in the form of a semi-graphitized carbon monolith comprising a hierarchized porous network free of mesopores and including macropores with a mean dimension $d_A$ of 1 μm to 100 μm, and micropores with a mean dimension $d_I$ of 0.5 nm to 2 nm, said macropores and micropores being interconnected. In said electrode, the macropores contain at least one electroactive species in direct contact with the semi-graphitized carbon that makes up the surface of the macropores. The invention also relates to a method for preparing such an electrode as well as to the use thereof as a biosensor or for manufacturing a biopile.

9 Claims, 6 Drawing Sheets

(51) Int. Cl.
  *C04B 38/00* (2006.01)
  *C12Q 1/26* (2006.01)
  *H01M 4/86* (2006.01)
  *H01M 4/90* (2006.01)
  *H01M 8/16* (2006.01)
  *B05D 5/00* (2006.01)
  *C04B 111/00* (2006.01)

(52) U.S. Cl.
  CPC ...... *H01M 8/16* (2013.01); *C04B 2111/00853* (2013.01); *C04B 2235/422* (2013.01); *C04B 2235/425* (2013.01); *Y02E 60/527* (2013.01)

(56) References Cited

U.S. PATENT DOCUMENTS

2009/0192297 A1* 7/2009 Yoshida et al. ............... 530/402
2011/0262993 A1* 10/2011 Backov et al. ............... 435/188

OTHER PUBLICATIONS

Designing highly efficient enzyme-based carbonaceous foams electrodes for biofuel cells.

Hard-Templating Approach Using Silica Si (Hype) Foams to Generate Micro-Macroporous Carbonaceous Monoliths.

Carbon coated monoliths as support material for a lactase from *Aspergillus oryzae:* Characterization and design of the carbon carriers.

Hard Macrocellular Silica Si (HIPE) Foams Templating Micro/Macroporous Carbonaceous Monoliths: Applications as Lithium Ion Battery Negative Electrodes and Electromechanical Capacitors.

Preparation of a carbon monolith with hierarchical porous structure by ultrasonic irradiation followed by carbonization, physical and chemical activation.

International Search Report dated Mar. 16, 2011.

* cited by examiner

ENZYMATIC MODIFICATIONS OF A CELLULAR MONOLITHIC CARBON AND USES THEREOF

RELATED APPLICATIONS

This application is a National Phase Application of PCT/FR2011/050093, filed on Jan. 19, 2011, which in turn claims the benefit of priority from French Patent Application No. 10 50361 filed on Jan. 20, 2010, the entirety of which are incorporated herein by reference.

BACKGROUND

1. Field of the Invention

The present invention relates to a porous electrochemical electrode consisting of a semi-graphitized carbon monolith comprising a hierarchical porous network comprising interconnected macropores and micropores, the macropores of which contain an electroactive entity, to a process for preparing such an electrode, and to the use of such an electrode as a biosensor for detecting analytes in a liquid medium or for producing a biofuel cell.

2. Description of Related Art

A biosensor is an analytical tool or system consisting of an immobilized biological entity, known as a "ligand", connected to a transducer which converts the biochemical signal into a quantifiable physical signal. According to the International Union of Pure and Applied Chemistry (IUPAC), a biosensor must be small and compact, have a reversible signal, give precise determinations ("onoff" reactions) and establish a real connection between the biological material and the transducer.

Electrochemical biosensors constitute a particular category of biosensors in which the ligand is immobilized on an electrode. In this case, the biochemical response to the addition of a substrate (analyte) is converted into an amplified and quantifiable electrical signal. Electrochemical biosensors may be amperometric, potentiometric, coulometric or conductimetric. Amperometric biosensors measure the current generated at a constant potential by an oxidoreduction reaction. Potentiometric biosensors measure the potential difference between an active electrode and a reference electrode. The ligands are biological compounds which make it possible to give the biosensor great specificity. The ligands most commonly used are enzymes and antibodies. However, whole cells, cell organelles, nucleic acids (DNA, RNA, oligonucleotides), antigens or alternatively receptors may also be used.

A biofuel cell is a system consisting of a cathode and an anode, to which bioelectrocatalysts of different nature (ligand) are attached, most often electroactive enzymes, the reactions of which with the substances present in the medium in which they are implanted generate an electric current which makes it possible to supply low-power equipment in varied fields such as the environment or health. By way of example of a biofuel cell, mention may in particular be made of the biofuel cells which use the chemical energy from the oxygen-glucose pair naturally present in physiological fluids to supply implanted medical devices intended, for example, to monitor blood glucose levels in diabetics. In this biofuel cell, a glucose oxidase is attached to the anode by means of a conductive polymer I and a bilirubin oxidase (BOD) is attached to the cathode by means of a conductive polymer II. When functioning, at the anode, the electrons are transferred from the glucose present in the physiological fluid to the glucose oxidase (GOx), and then from the GOx to the conductive polymer I and from the conductive polymer I to the anode. At the cathode, the electrons are transferred from the cathode to the conductive polymer II, then to the BOD and from the HOD to the oxygen present in the physiological fluid.

Irrespective of the application envisioned (electrochemical biosensor or biofuel cell), the ligand can be immobilized on the electrode by various, methods, such as adsorption, covalent coupling, encapsulation, etc.; the objective of any immobilization method is to retain the maximum activity of the biological ligand on the surface or in the porosity of the electrode. The selection of a suitable immobilization method depends on the nature of the biological ligand, on the type of electrode used, on the physicochemical properties of the analyte to be detected and on the operating conditions of the electrochemical system. The two methods most commonly used are adsorption and covalent coupling. The physical adsorption of a ligand based on Van Der Waals attractive forces is the oldest and simplest method of immobilization. It does not require any chemical modification of the ligand and makes it possible to regenerate the biosensor or the biofuel cell. The major advantage of this method is its simplicity. However, loss of adsorbed ligand is possible if changes in pH, in ionic strength or in temperature occur during the measurements carried out with the biosensor or the operating of the biofuel cell. Covalent coupling can be used to allow immobilization on a matrix or directly at the surface of an electrode. These methods are based on the reaction between a functional, group of the ligand and reactive groups of the surface of the electrode, most commonly by means of a redox mediator. Indeed, in most biosensors and biofuel cells, the redox centers of enzymes are too far from the surface of the electrode to provide good conductivity of electrons and must be connected to the electrodes by means of redox mediators. The latter play the role of an electron shuttle between the biomolecule and the electrode. The redox mediators may, for example, consist of an electrically conducting linker arm. By way of example, mention may be made of U.S. Pat. No. 5,089,112, which describes a biosensor consisting of a current collector (carbon electrode) connected to a redox enzyme by means of a flexible siloxane comprising a ferrocene group.

One of the difficulties encountered during the production of such biosensors therefore lies in the development of these redox mediators. One of the major issues in this research field therefore consists in managing to directly connect the biomolecules to the surface of the electrodes in order to dispense with the redox mediator.

In order to be able to do without redox mediator, the electrode material must combine several obligatory criteria:
- be a conductive material with a large specific surface area, greater in particular than that of conventional carbon fibers,
- having an adjustable porosity in order to allow attachment of the enzyme by impregnation and diffusion of the enzyme substrates,
- be biospecific for electrochemical reactions in reasonable potential ranges in a biological medium and with respect to biomolecules or entities dissolved in biological media,
- be biocompatible.

Carbon is a material of choice for preparing electrodes. Its chemical inertia in fact makes it possible to explore large ranges of potentials in electrochemistry. For this reason, carbon is very widely used in various forms for preparing electrochemical devices: sensors, actuators, batteries and storage batteries. Furthermore, carbon has the particularity of being a material onto which organic molecules and polymers are effectively adsorbed. It is therefore possible to adsorb thereon redox mediators, enzymes or else conductive polymers for preparing advanced, effective and selective electrochemical devices. Carbon is, in addition, a biocompatible material, which lends itself ideally to the production of devices for biological applications. Carbon has other advantageous properties, which are mechanical strength, thermal stability and an ability to be formed on large scales (discs, films, monoliths of varied shapes).

Carbon electrodes are generally in the form of mesoporous materials. However, the performance levels of the present materials are further limited by currents of which the intensity is too low, by adsorptions which are not very stable or not effective enough and by kinetic limitations due to a low mass transport when the materials are strictly mesoporous. For example, in the case of biofuel cells, the powers generated are insufficient for biomedical devices, such as the supply of electricity to implanted biosensors, in particular.

Increasing the current density of a biosensor or of a biofuel cell is an imperative step for being able to achieve, respectively, sufficient detection limits or powers greater than 2 µW. To do this, it is necessary to increase the specific surface area of the electrodes while at the same time maintaining a sufficient mass transport.

Patent application US 2007/0062821 describes an electrically conducting porous carbonaceous material of which the pores are functionalized with a redox enzyme. The material used in this case consists of a porous metal framework called "metal foam" (metals and metal alloys chosen from Ni, Cu, Ag, Au, Ni/Cr for example), the surface of which is ac least partly covered with a carbonaceous material such as a carbon powder (Ketjenblack in particular), carbon nanotubes or a fullerene. In this type of support, the immobilization of the enzymes can be carried out without using a redox mediator; however, the metals used to produce the framework of this device and the carbon nanotubes covering it are not biocompatible. The productivity of such a device is, moreover, only 4 mA/cm$^2$, which is still not satisfactory.

Materials which are in the form of porous carbon monoliths constitute materials of choice for numerous applications such as water and air purification, adsorption, heterogeneous-phase catalysis, the production of electrodes that can be used as a biosensor or as biofuel cells, and energy storage, owing to their large specific surface area, to their large pore volume, to their insensitivity to the surrounding chemical reactions, to their excellent mechanical properties and, finally, to their biocompatibility.

These materials comprise a high specific surface area and a hierarchical structure, i.e. a cellular structure generally exhibiting a double porosity. They exhibit in particular a mesoporous structure in which the mean pore diameter varies from about 2 to 10 nm.

They can be prepared according to two main families of processes.

The first main family of processes uses soft templates and corresponds to the soft templating methods, i.e. to the methods employing organic/organic interactions between a thermopolymerizable polymer (generally carbon precursor) and certain block copolymers of nonionic polymer type, such as the products sold under the trade names Pluronic® P123 or F127 by the company BASF, which are used as modeling agent in order to directly obtain a porous carbonaceous material after carbonization under an inert atmosphere at 350° C. and pyrolysis (Meng Y. et al., Angew. Chem. Int. Ed., 2005, 44, 2).

The second main family of processes uses rigid templates and corresponds to the hard templating or exotemplating methods, i.e. to the methods in which a mesoporous solid template is impregnated with a solution of a precursor of the final material which it is desired to obtain (carbon precursor, for example), before being carbonized under a nonoxidizing atmosphere.

OBJECTS AND SUMMARY

The invention which will be described hereinafter uses materials prepared according to a process belonging to the family of hard templating methods.

The inventors have now discovered that the use, as an electrode, of a cellular carbon monolith comprising a porous network free of mesoporosity while at the same time having a large specific surface area makes it possible to dispense with the use of a redox mediator, thus making it possible to produce biosensors and biofuel cells which are effective, in particular in terms of current density, without it being necessary to use a redox mediator to pass the electrons between the electroactive entity and the electrode. As is demonstrated in the examples illustrating the present application, the electrochemical electrodes obtained from the carbon monoliths that can be used according to the present invention are even more effective when the electroactive entity is in direct contact with the constituent semi-graphitized carbon of the monolith than when a redox mediator is used to make the junction between the electroactive entity and the constituent semi-graphitized carbon of the monolith.

A subject of the present invention is therefore a porous electrochemical electrode characterized in that it consists of a solid cellular material provided in the form of a semi-graphitized carbon monolith comprising a hierarchical porous network free of mesopores and comprising macropores with a mean dimension $d_A$ of from 1 µm to 100 µm, and micropores with a mean dimension $d_I$ of from 0.5 to 2 nm, said macropores and micropores being interconnected, and in that the macropores contain at least one electroactive entity in direct contact with the semi-graphitized carbon chat makes up the surface of the macropores.

The term "monolith" is intended to mean a solid object with an average dimension of at least 1 mm.

The term "mesopore" is intended to mean any pore of which the mean diameter ranges from 2 to 50 nm approximately.

The term "electroactive entity" is intended to mean any molecule in which an electron exchange can take place, i.e. any molecule which can donate or accept one or more electrons.

According to the invention, the expression "in direct contact" used to qualify the electroactive entity means that said entity is immobilized at the surface of the macropores of the semi-graphitized carbon monolith without the use of a redox mediator, i.e. it is not necessary to use an electrically conducting linker arm to attach the electroactive entity to the surface of the macropores.

Through the use of such a carbon monolith as electrode material, the electrochemical electrode in accordance with the invention has the following advantages:
  it has a large specific surface area, greater in particular than that of conventional carbon fibers;
  it is possible to modulate the pore diameter according to the nature of the electroactive entity that it is desired to immobilize and of the corresponding analyte;
  it is biospecific with respect to biomolecules or entities dissolved in a liquid medium, for example in a physiological fluid;

the electroactive entity is immobilized at the surface of the macropores without using any electrically conducting linker arm, i.e. without using a redox mediator;

the electroactive entities immobilized in the macropores of the monolith retain all of their biological activity;

the macropores allow rapid impregnation of electrolytes within the electrode, the associated impregnation kinetics are not limited by Fick's diffusion;

good mechanical properties.

According to one preferred embodiment of the invention, the walls of the macropores of the semi-graphitized carbon monolith have a thickness of from 0.5 to 40 μm and preferably from 2 to 25 μm.

The macropores preferably have a diameter of from 4 to 70 μm approximately.

According to the invention, the micropores are present in the thickness of the walls of the macropores, therefore making them microporous. The micropores preferably have a diameter of from 0.7 to 1.5 nm approximately.

The specific surface area of the semi-graphitized carbon monolith that can be used in accordance with the invention is generally from 400 to 900 m²/g approximately, preferentially from 500 to 700 m²/g approximately.

The porous semi-graphitized carbon monoliths that can be used according to the present invention can be prepared according to a process comprising at least the following steps:

1) a step of preparation of a solid silica template in the form of a cellular monolith consisting of a matrix of silica or of organically modified silica, said monolith comprising macropores with a mean dimension $d_A$ of from 1 μm to 100 μm, mesopores with a mean dimension $d_E$ of from 2 to 50 nm and micropores with a mean dimension $d_I$ of from 0.5 to 2 nm, said pores being interconnected;

2) a step of impregnation, under vacuum, of the solid silica template with a solution of at least one carbon precursor;

3) a step of polymerization and/or oz crosslinking of said precursor within the solid silica template;

4) a step of carbonization of the solid, silica template containing said polymerized and/or crosslinked precursor, said step being carried out as a temperature greater than or equal to 700° C. in order to result in semi-graphitization of the carbon;

5) the production of said semi-graphitized carbon monolith by removal, of the solid silica template by treatment with an acid or a base, said treatment being carried out without distinction before or after said carbonization step.

For the purpose of the present invention, the term "mesoporous network" is intended to mean a network comprising mesopores, i.e. pores of which the size varies from 2 to 50 nm.

The preparation of the silica template, during the first step, is preferably carried out according to the processes as described in patent applications FR-A1-2 852 947 and FR-A1-2 912 400. These processes generally consist in preparing an emulsion by introducing an oily phase into an aqueous solution of surfactant, adding an aqueous solution of at least one silica oxide precursor and/or of at least one organically modified silica oxide precursor to the solution of surfactant, before or after preparation of the emulsion, leaving the reaction mixture to stand until said precursor has condensed, then drying the mixture in order to obtain the expected solid silica template.

In this case, the silica oxide or organically modified silica oxide precursor(s) may be chosen from silica tetralkoxides of the following formula (I):

$$R'_n(OR)_{4-n}Si \qquad (I)$$

in which:

R represents an alkyl radical having from 1 to 5 carbon atoms or an organic group of the following formula (II):

$$-(CH_2)_m-R_1 \qquad (II)$$

in which 0≤m≤5, and $R_1$ is chosen from a thiol group, a pyrrol group, an amino group which optionally bears one or more optionally substituted alkyl, alkylamino or aryl substituents, an alkyl group (preferably having from 1 to 5 carbon atoms), or a phenyl group which optionally bears a substituent. $R_2$ of alkyl type, in particular a methyl group, R' represents an alkyl radical having from 1 to 5 carbon atoms or an aryl radical which optionally bears one or more functional groups, and 0≤n<m; m being the valence of the silicon atom.

In particular, the organic group of formula (II) may be:

a 3-mercaptopropyl croup;

a 3-aminopropyl group;

an N-(3-propyl)pyrrol group;

an N-(2-aminoethyl)-3-aminopropyl group;

a 3-(2,4-dinitrophenylamino)propyl group;

a phenyl or benzyl group; or a methyl group.

The precursor(s) of formula (I) is (are) preferably chosen from tetramethoxysilane, tetraethoxyorthosilane (TEOS), (3-mercaptopropyl)trimethoxysilane, (3-amino-propyl)triethoxysilane, N-(3-trimethoxysilylpropyl)-pyrrol, 3-(2,4-dinitrophenylamino)propyltriethoxysilane, N-(2-aminoethyl)-3-aminopropyltrimethoxysilane, phenyltriethoxysilane and methyltriethoxysilane.

The use of a precursor of formula (I) comprising at least one group of formula (I) makes it possible to obtain a silica template in which the wetting with the solution of carbon precursors is improved. This also makes it possible to optimize the impregnation of the porosity with polymerizable monomers or with macromonomers which will give rise to the carbon.

The concentration of silica oxide precursor(s) and/or of organically modified silica oxide precursors within the aqueous solution is preferably greater than 10% by weight, relative to the weight of the aqueous phase. This concentration varies more preferentially from 17 to 35% by weight relative to the weight of the aqueous phase.

The oily phase preferably consists of one or more compounds chosen from linear or branched alkanes having at least 12 carbon atoms. By way of example, mention may be made of dodecane and hexadecane. The oily phase may also consist of a silicone oil with a low viscosity, i.e. less than 400 centipoises.

The amount of oily phase present within the emulsion can be adjusted according to the diameter of the macropores which it is desired to obtain for the silica template, it being understood that the greater the oil/water fraction by volume, the smaller the diameter of the oil droplets within the emulsion and also the smaller the diameter of the macropores.

Generally, the oily phase represents from 60 to 90% by volume relative to the total volume of the emulsion. This amount of oil makes it possible to obtain a silica template in which the mean diameter of the macropores varies from 1 to 100 μm approximately.

The surfactant compound may be a cationic surfactant chosen in particular from tetradecyltrimethylammonium bromide (TTAB), dodecyltrimethylammonium bromide or cetyltrimethylammonium bromide. When the surfactant compound is cationic, the reaction medium is brought to a pH of less than 3, preferably less than 1. Tetradecyltrimethylammonium bromide is particularly preferred.

The surfactant compound may also be an anionic surfactant chosen from sodium dodecyl sulfate, sodium dodecyl sulfonase and dioctyl sodium sulfosuccinate (AOT). When the surfactant compound is anionic, the reaction medium is brought to a pH of greater than 10.

Finally, the surfactant compound may be a nonionic surfactant chosen from surfactants comprising an ethoxylated head, and nonylphenols. Among such surfactants, mention may in particular be made of ethylene glycol and propylene glycol block copolymers sold, for example, under the trade names Pluronic® P123 and Pluronic® F127 by she company BASF. When the surfactant compound is nonionic, the reaction medium is brought to a pH of greater than 10 or less than 3, preferably less than 1, and, in addition, preferably contains sodium fluoride in order to improve the condensation of the silica oxide precursors.

The total amount of surfactant present within the emulsion can also be adjusted according to the diameter of the macropores that it is desired to obtain in the silica template. This amount can also be varied according to the nature of the surfactant used.

Generally, the amount of surfactant ranges from 1 to 10% by weight, preferably from 3 to 6% by weight, relative to the total weight of the emulsion.

The step of condensation of the silica oxide precursor(s) and/or of the organically modified silica oxide precursor(s) is advantageously carried out at a temperature close to ambient temperature. The duration of this, step can vary from a few hours (2 to 3 hours) to a few weeks (2 to 3 weeks) depending on the pH of the reaction medium.

The silica template obtained at the end of the first step is preferably washed using an organic solvent (such as, for example, tetrahydrofuran, acetone and mixtures thereof), and then dried (for example with air in an oven or by lyophilization), before being subjected to the step of impregnation with the solution of carbon precursor or of ceramic precursor.

The carbon precursor(s) is (are) preferably chosen from phenolic resins, resorcinols, styrene, divinylbenzene, polysaccharides, such as, for example, sucrose and its derivatives, potato starch, lignin, lignin-cellulose mixtures and petroleum pitches.

The carbon precursors may be provided in the form of monomers, of oligomers, of preformed macromonomers or of polymers which are polymerized and/or crosslinked during step 3). When a petroleum pitch is used as carbon precursor, step 3) is not necessarily carried out.

The precursor of the impregnation solution is preferably a carbon precursor, and even more preferentially a phenolic resin, in particular a phenol/formaldehyde resin.

The solvent of the solution of carbon precursor is preferably an organic solvent chosen from lower alcohols, such as ethanol, tetrahydrofuran (THF), toluene, and mixtures thereof. When the carbon precursor is chosen from phenolic resins, the solvent may also be chosen from water and mixtures of water with at least one organic solvent chosen from the abovementioned solvents, in the presence of a base.

The amount of carbon precursor in the solution used for the impregnation step can be adjusted according to the diameter of the macropores that it is desired to obtain in the carbon monoliths at the end of the process, it being understood that the lower this amount, the greater the diameter of the macropores and the finer the internal junctions (walls of the macropores). Generally, the amount of carbon precursor within the impregnation solution varies from 5% to 90% by weight, and even more preferentially from 20% to 70% by weight, relative to the total weight of said solution.

Step 3) of polymerization and/or crosslinking of the carbon precursor(s) can be carried out by any methods known to those skilled in the art.

When the precursor is a carbon precursor, such as, for example, a phenolic resin, a thermocrosslinking is carried out.

When the precursor is a carbon precursor such as for example, styrene or divinylbenzene, a crosslinking is carried out which is induced by a crosslinking agent chosen in particular from azo(bis)isobutyronitrile (AIBN), potassium peroxodisulfate and sodium peroxodisulfate.

The step of carbonization of the silica template impregnated with carbon precursor makes it possible to obtain semi-graphitized carbon and is generally carried out in a reducing atmosphere, at a temperature varying from 700 to 1200° C. approximately, for a period of time of from 3 to 12 hours approximately.

As previously indicated, the step of removal of the silica template can be carried out without distinction before or after the carbonization step, the order in which these two steps are carried out having in fact no effect on the structure of the porous network of the resulting monolith.

This step of removal of the silica template is preferably carried out by immersion of the silica template impregnated with polymerized and/or crosslinked precursor, or of the carbon monolith resulting from the carbonization, in a solution of an acid, such as, for example, a hydrofluoric acid solution, or in a basic solution having a pH greater than 9, such as, for example, in a sodium hydroxide or potassium hydroxide solution. The duration of this treatment is not critical, from the moment at which it results in the complete removal of she silica template. This duration generally varies from 12 to 24 hours.

The electroactive entities that can be immobilized in the macropores of the semi-graphitized carbon monolith that can be used according to the invention may be chosen from all molecules in which an electron exchange is possible. Among such molecules, mention may be made of enzymes comprising a redox center, nucleic acids such as DNA, RNA and oligonucleotides, antibodies and antigens, and also conductive polymers such as polypyrroles, polyanilines and redox polymers.

For the purpose of the present invention, the expression "enzyme comprising a redox center" is intended to mean any enzyme capable of catalyzing an oxidation or reduction reaction.

According to one preferred embodiment of the invention, the electroactive entity is an enzyme comprising a redox center and is chosen from oxidoreductases (E.C.1) comprising in particular:

i) oxidases such as glucose oxidases, glucose-6-phosphate dehydrogenases, isocitrate dehydrogenases, lactate dehydrogenases, xanthine oxidases, lactate oxidases, pyruvate oxidases, bilirubin oxidase, laccases, cholesterol oxidases, glutamate oxidases, pyruvate oxidases and peroxidases such as horseradish peroxidase;

ii) reductases such as 5-alpha reductases, cytochrome b5 reductases, folate and dihydrofolate reductases, HMG-CoA reductase (or 3-hydroxy-3-methylglutaryl-CoA reductase HMGR), glutathione reductase, methemoglobin reductase and ribonucleotide reductase;

iii) oxygenases comprising monooxygenases such as lipoxygenase and dioxygenases such as cinnamate 4-hydroxylase, phenylalanine hydroxylase, tyrosine hydroxylase, tyrosinase, cyclooxygenase, heme oxidase and cytochrome P450;

iv) hydrogenases and dehydrogenases such as, for example, glucose dehydrogenases, glutamate dehydrogenases, and luciferases.

In order to function, these oxidoreductase enzymes are associated with cofactors chosen from oxidoreduction coenzymes such as, for example, nicotinamide adenine dinucleotide (NAD), nicotinamide adenine dinucleotide phosphate (NADP), flavin adenine dinucleotide (FAD), flavin mononucleotide (FMN), heme, and pyrroloquinoline quinone (PQQ), or alternatively with metal cations.

Thus, when the electroactive entity is an oxidoreductase, then the macropores of the carbon monolith contain at least one cofactor chosen from oxidoreduction coenzymes (it being possible for said cofactor to be an integral part of the oxidoreductase enzyme, i.e. a portion of the enzymatic protein itself, or else to be present in a separate form) and metal cations.

According to one preferred embodiment of the invention, the amount of immobilized electroactive entity varies from 0.01 to 7% by weight approximately and more preferentially from 0.04 to 3% by weight approximately, relative to the total weight of the electrochemical electrode.

The electroactive entities are immobilized within the macropores of the constituent semi-graphitized carbon monolith of the electrochemical electrode in accordance with the invention by means of electrostatic interactions with the semi-graphitized carbon (adsorption), and also via steric constraints related to the size of the macropores.

The very strong interaction of the semi-graphitized carbon with the electroactive entity or entities provides increased adsorption stability. This stability is critical for the stability of the corresponding biosensors and biofuel cells. This is because this increased stability guarantees an operating time that is much longer than that which can be obtained with conventional carbonaceous materials.

A subject of the present invention is also a process for preparing an electrochemical electrode in accordance with the invention and as defined above, said process being characterized in that it comprises a step of impregnation of a semi-graphitized carbon monolith comprising a hierarchical porous network free of mesopores and comprising macropores with a mean dimension $d_A$ of from 1 μm to 100 μm, and micropores with a mean dimension $d_I$ of from 0.5 to 2 nm, said macropores and micropores being interconnected, with an aqueous solution or an aqueous dispersion of at least one electroactive entity, it being understood that said process does not comprise a step of functionalization of the surface of the macropores with a redox mediator.

The monolith impregnation step is preferably carried out under vacuum.

According to one particularly preferred embodiment, the impregnation step is carried out under vacuum, at ambient temperature for a period of time of approximately 72 hours.

When the electroactive entity is an oxidoreductase enzyme, and the cofactor is an oxidoreduction coenzyme which is not an integral part of the enzyme, or metal cations, then the aqueous solution or the aqueous dispersion used to impregnate the semi-graphitized carbon monolith also comprises at least one oxidoreduction coenzyme or metal cations.

The washing of the monolith at the end of the impregnation step is preferably carried out with distilled water.

A subject of the invention is also the use of an electrochemical electrode as defined previously, as a biosensor for detecting analytes in a liquid medium or for producing a biofuel cell.

When the electrode in accordance with the invention is used as a biosensor, the nature of the analytes that may be detected will of course vary according to the nature of the electroactive entity immobilized in the macroporosity of the semi-graphitized carbon monolith.

By way of example, when the immobilized entity is a glucose oxidase, the electrochemical electrode may then be used as a biosensor for detecting the glucose level in a liquid medium and in particular in a biological fluid such as blood.

When the immobilized entity is a nucleic acid molecule or a protein, the electrochemical electrode may then be used as an affinity biosensor, the operating of which is based on oligonucleotide-DNA and/or antigen-antibody biological recognition. This type of biosensor can be used as a tool, for instance in medical diagnosis (cancer markers).

Biofuel cells are fuel cells which are based on biocatalytic reactions at the electrodes in order to convert the chemical fuels present in the biological media of human beings into electric power. A biofuel cell can, for example, serve as a source of energy for supplying medical devices implanted in the human body, for example an implant intended to measure and transmit the blood sugar level.

When the electrode in accordance with the invention is used for producing a biofuel cell, said biofuel cell may, for example, consist of a first electrode in accordance with the invention (anode) in which the immobilized entity is a glucose oxidase and of a second electrode in accordance with the invention (cathode) in which the immobilized entity is bilirubin oxidase, the two electrodes being connected to one another via an electric circuit passing through a device to be supplied with electrical energy.

The immobilization of the enzymes in the materials mentioned makes it possible to avoid the presence of a membrane for separating the two compartments of the biofuel cell, thus making it possible to simplify the device and making it possible to miniaturize said device.

Another subject of the invention is a biosensor characterized in that it comprises at least one electrochemical electrode in accordance with the invention and as described above.

Finally, a subject of the invention is a biofuel cell comprising a positive electrode and a negative electrode connected to one another via an electric circuit, said biofuel cell being characterized in that at least one of the two electrodes is an electrochemical electrode in accordance with the invention and as described above.

DETAILED DESCRIPTION

Figure 1:
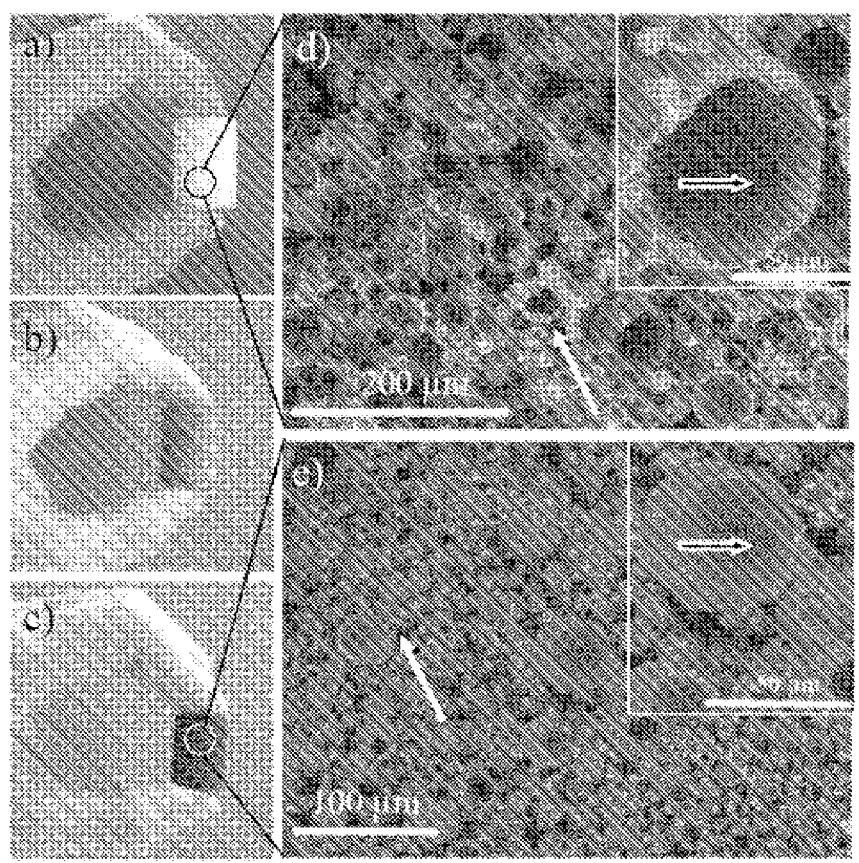
FIGS. 1a-1e show views of monoliths obtained in example 1, in accordance with one embodiment.

The present invention is illustrated by the following exemplary embodiments, to which it is non, however, limited.

EXAMPLES

The raw materials used in the examples which follow are listed hereinafter:
98% tetradecyltrimethylammonium bromide (TTAB): the company Alfa Aesar;
98% tetraethoxyorthosilane (TEOS): the company Aldrich;
acetone and dodecane at 99%: the company Rectapur;
tetrahydrofuran (THF); 48% hydrofluoric acid and 37% hydrochloric acid: the company Analar Normapur;
phenol/formaldehyde resin, sold under the name Ablaphene® RS 101 by the company Rhodia;
bilirubin oxidase (ROD) sold by the company Amano (Japan);
redox polymer: copolymer of polyacrylamide and of poly (N-vinylimidazole) complexed with [Os (4,4'-dichloro-2,2'-bipyridine)$_2$Cl]$^{+/2+}$ (PAA-PVI-bipy). The PAA-PVI copolymer can be prepared as follows: 4,4'-dinitro-2,2'-bipyridine N,N'-dioxide was prepared as described by Anderson, S. at al., J. J. Chem. Soc., Dalton Trans. 1985, 2247-2250, and Kenausis G. et al., A. J. Chem. Soc., Faraday Trans, 1996, 92, 4131-4135. 4,4'-Dichloro-2,2'-bipyridine (dcl-bpy) was then synthesized from the 4,4'-dinitro-2,2'-bipyridine N,N'-dioxide according to the method modified by Maerker G. et al. (see Anderson, S. et al., above and Maerker G. et al., J. Am. Chem. Soc. 1958, 80, 2475-2477). Os(dcl-bpy)$_2$Cl$_2$ was prepared as follows (NH$_4$)$_2$OsCl$_6$ and "dcl-bpy" were dissolved in ethylene glycol in a 1:2 molar ratio and brought to reflux under argon for 1 hour (yield 85%). Os(dcl-bpy)$_2$Cl$_2$ was then complexed with the 1:7 polyacrylamide/poly(N-vinylimidazole) (PAA-PVI) copolymer and purified as described by Zakeeruddin, S. M. et al., J. Electroanal. Chem. 1992, 337, 253-256, so as to produce the redox polymer PAA-PVI-bipy;
polyethylene glycol diglycidyl ether sold under the name (PEGDGE)-400 by the company Polysciences.

The commercial raw materials were used as received from the manufacturers, without further purification.

The various monoliths obtained in the examples were characterized on various size scales.

The mesoporosity was characterized qualitatively by means of a transmission electron microscopy (TEM) technique using a Jeol 2000 FX microscope with an accelerating voltage of 200 kV. The samples were prepared by depositing powdered silica skeletons on a copper grid coated with a Formvar@ carbon membrane.

The macroporosity was characterized qualitatively by means of a scanning electron microscopy (SEM) technique using a Jeol JSM-840A scanning microscope which operates at 10 kV. The samples were coated with gold or carbon before their characterization.

The specific surface area measurements were carried out by means of nitrogen adsorption/desorption techniques using a device sold under the name Micromeritics ASAP 2010; the interpretation being carried out by the BET or BJH calculation methods.

The macroporosity was quantified by mercury intrusion measurements, using a device sold under the name Micromeritics® Autopore IV, in order to achieve the characteristics of the macroscopic inorganic cells of which the inorganic skeleton is composed.

The samples were subjected to analysis by X-ray diffraction (XRD) or by small-angle X-ray diffraction (SAXs), using an 18 kW rotating anode X-ray source (Rigaku-200) employing a Ge crystal (111) as monochromator. The scattered radiation was collected on a two-dimensional collector (Imaging Plate system, sold by Mar Research, Hamburg). The distance from the detector to the sample was 500 mm.

Thermogravimetric analyses were carried out under an oxygen stream (5 cm$^3$·min$^{-1}$) using a thermogravimetric analyzer sold under the name Stearam TAG-1750.

Fourier transform infrared spectroscopy (FTIR) analyses were carried out on a spectrometer sold under the name Nicolet 750.

Mechanical compression tests were carried out using a device sold under the name Instron 4466. The samples were compressed between two rigid plates and the mechanical strains observed at various pressures were recorded. The compression rate was 0.5 mm/s.

Example 1

Preparation of Macro- and Microporous Carbon Monoliths

In this example, the preparation of various carbon monoliths exhibiting a double macro/micro porosity starting from a micro/meso/macroporous silica monolith is illustrated.
1) First Step:
Synthesis of a Micro/Meso/Macroporous Silica Monolith (MSi)
5 g of TEOS were added to 16 g of a 35% aqueous solution of TTAB acidified beforehand with 7 g of HCl. Hydrolysis was allowed to take place until a single-phase hydrophilic medium was obtained (aqueous phase of the emulsion). 35 g of dodecane (oily phase of the emulsion) were then added, dropwise and with stirring, to this aqueous phase. The emulsion was then left to condense in the form of a silica monolith for one week at ambient temperature. The silica monolith thus synthesized was then washed with a THF/acetone (50/50:v/v) mixture in order to extract the oily phase therefrom. The silica monolith was then dried for one week at ambient temperature and then it was subjected to a heat treatment at 650° C. for 6 hours, a rate of rise in temperature of 2° C./min being applied, with a plateau at 200° C. for 2 hours. A silica monolith was obtained which was designated MSi.
2) Second Step:
Impregnation of the Silica Monolith with the Phenolic Resin
The silica monolith MSi obtained above was cut into 5 identical pieces, each of 0.5 g, using a hand saw.

Moreover, the following four solutions of Ablaphene® RS 110 phenolic resin were prepared:
solution S25: Ablaphene® RS 110 at 25% by weight in THF,
solution S60: Ablaphene® RS 110 at 65% by weight in THF,
solution S80: Ablaphene® RS 110 at 80% by weight in THF,
solution S90: Ablaphene® RS 110 at 90% by weight in THF.

A 0.5 g piece of silica monolith was then immersed in each of the solutions S25 to 390 in a beaker. The beakers were placed under vacuum until the effervescence had disappeared, in order to ensure good impregnation of the silica matrices by the phenolic resin solutions. After stirring at ambient temperature for 24 hours, each of the solutions was filtered.

The silica monoliths thus impregnated with the solutions S25 to S90, respectively MSiS25, MSiS60, MSiS80 and MSiS90, were then quickly washed with THF and then dried in an oven at a temperature of 80° C. for 24 hours in order to facilitate the evaporation of the solvent and to thermally initiate the crosslinking of the monomers of the phenolic resin. Each of the monoliths MSiS25 to MSiS90 was then subjected to a second heat treatment in a hot-air oven at 155° C. for 5 hours, with a rate of rise in temperature of 2° C./min, a first plateau at 80° C. being produced for 12 hours and then a second plateau at 110° C. being produced for 3 hours. The monoliths were then allowed to return to ambient temperature by simply switching off the oven. Silica monoliths impregnated with a crosslinked phenolic resin (hybrid monoliths of MSiScross type) were thus obtained. These monoliths are respectively denoted. MSiS25cross, MSiS60cross, MSiS80cross and MSiS90cross. The MSiS80cross monolith was prepared in duplicate.

3) Third Step:

Synthesis of the Carbon Monoliths

Two synthesis routes were implemented.

According to the first synthesis route, each of the monoliths MSiS25cross, MSiS60cross, MSiS80cross and MSiS90cross as obtained above at the end of the second step was immersed in three successive baths of 10% hydrofluoric acid and then washed thoroughly with deionized water. This treatment with hydrofluoric acid resulted in the removal of the silica template. The monoliths resulting from this treatment were then dried in a hot-air oven at 80° C. overnight. After drying, the monoliths were subjected to pyrolysis at a temperature of 900° C. for 1 hour under a nitrogen stream while observing a rate of rise in temperature of 4° C./min. The graphitized carbon monoliths thus obtained are respectively denoted MS25carb, MS60carb, MS80carb and MS90carb.

The second synthesis route, was applied to the other monolith. MSiS80cross. According to this second route, the order in which the treatment with hydrofluoric acid and the pyrolysis were carried out was simply reversed, each of these two steps being nevertheless carried out in a manner identical to the procedure used to produce the MScarb monoliths. The resulting graphitized carbon monolith was referred to as MS80HF.

4) Characterizations

The appended FIG. 1 shows macroscopic views of the monoliths obtained at the end of each of the three steps of the process: FIG. 1a) corresponds to a monolith of MSi type; FIG. 1b) corresponds to a monolith of MSiScross type and FIG. 1c) corresponds to a carbon monolith of MS80HF type.

It is noted that the general shape of the silica monolith used as template is reproduced exactly by the carbon monolith via the hybrid monolith of MSiScross type. A loss of volume of approximately 45% between the silica monolith, and the corresponding carbon monolith is also observed; this loss of volume is due to a type of settling of the material brought about by the removal of the silica template during the pyrolysis.

The appended FIG. 1 also shows a microscopic SEM view of the macroscopic porous network of a monolith of MSi type (FIG. 1d) and of the carbon monolith of MS80HF type. In these figures, the white arrows indicate the external junctions of the pores and the black arrows on a white background indicate the internal junctions of the pores.

It is observed that the structure of the macroporous network of the silica monolith is retained in the corresponding carbon monolith, indicating chat the latter is indeed the substantially exact replica of the silica template used, and not its negative.

The results of the mercury intrusion measurements carried out on each of the carbon monoliths synthesized in this example are given in the appended FIG. 2, and are collated in table 1 below.

Figure 2:
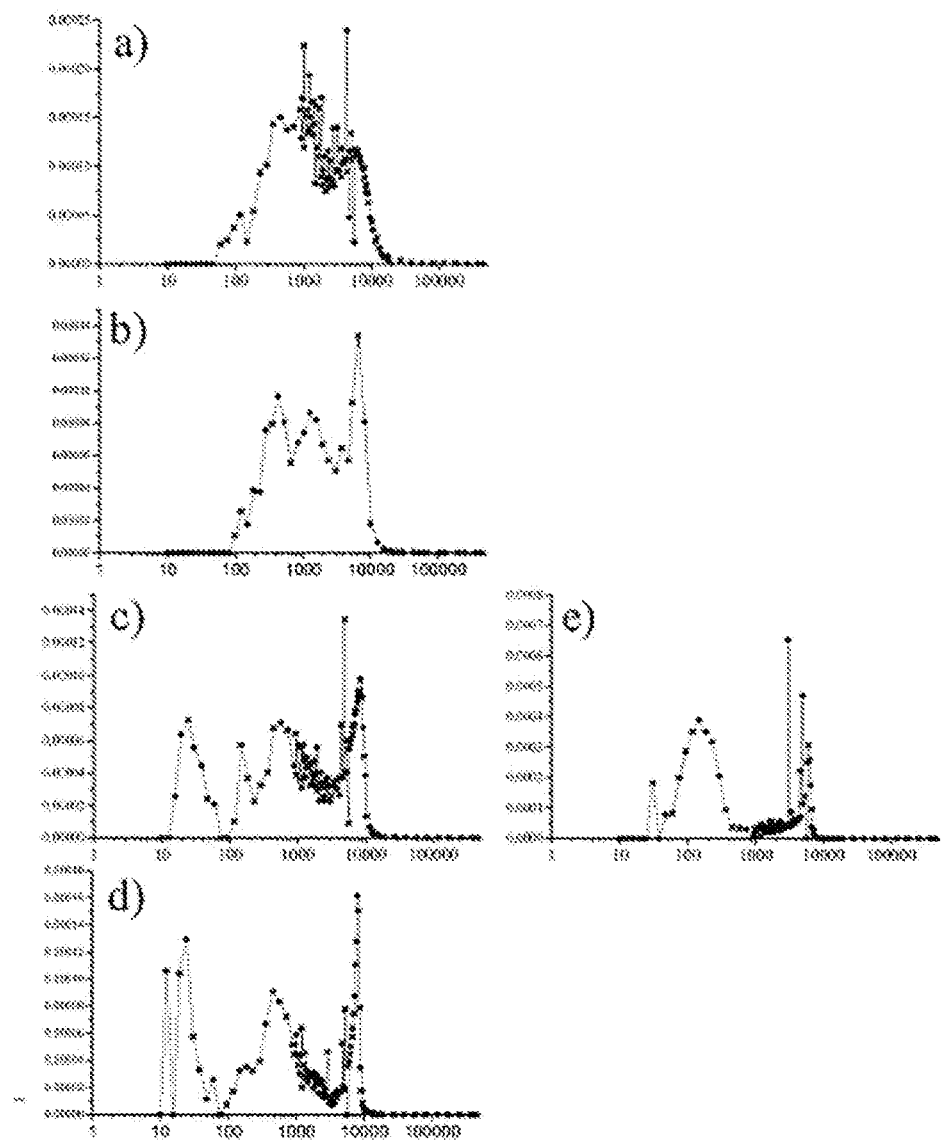
FIGS. 2a-2e show the results of mercury intrusion measurements carried out on each of carbon monoliths obtained in example 1, in accordance with one embodiment.

In FIG. 2, the curves 2a) to 2e) represent the differential intrusion volume (in mL/g/nm) as a function of the pore diameter (in nm) for each of the carbon monoliths (FIG. 2a): MS25carb; FIG. 2b): MS60carb; FIG. 2c) MS80carb; FIG. 2d) MS90carb and FIG. 2e) MS80HF).

TABLE 1

| Monoliths | MS25carb | MS60carb | MS80carb | MS80HF | MS90carb |
|---|---|---|---|---|---|
| Intrusion volume ($cm^3 \cdot g^{-1}$) | 1.4 | 1.0 | 0.6 | 0.7 | 0.5 |
| Porosity (%) | 71 | 58 | 51 | 48 | 42 |
| Bulk density ($g \cdot cm^3$) | 0.5 | 0.6 | 0.8 | 0.7 | 0.9 |
| Density of the skeleton ($g \cdot cm^3$) | 1.7 | 1.5 | 1.6 | 1.4 | 1.5 |

These results show that the volume of the macroporous network is inversely proportional to the concentration of the phenol/formaldehyde resin used to impregnate the MSi monolith (decrease in the intrusion volume and in the porosity percentage when going from MS25carb to MS90carb). The diameter of the macropores is polydispersed and varies from 10 to 10 000 nm (FIG. 2).

NB: The mercury impregnation measurements are only valid within the range of the macropores. The viewpoints which appear in the region of diameters of between 2 and 50 nm in FIGS. 2c and 2d in particular are measurement artifacts or point defects of the materials but do not under any circumstances correspond to the presence of a mesoporous network. Furthermore, the absence of mesoporous network has been confirmed by nitrogen adsorption/desorption measurements (see table 2 and conclusion for table 2 hereinafter).

The final density of the carbon skeleton of each of the monoliths is, on the other hand, substantially identical in each of the cases, owing to the fact that the skeleton consists exclusively of partially graphitized carbon.

The results obtained with MS80carb and MS80HF are not significantly different, which demonstrates that the two synthesis routes used during the carbonization step 3) are equivalent.

Figure 3:
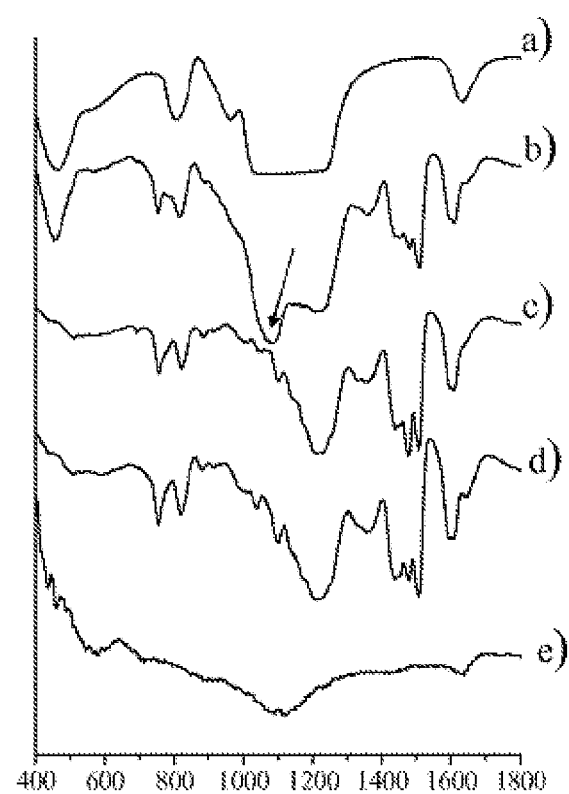
FIG. 3 is an FITR spectra for monoliths obtained in example 1, in accordance with one embodiment.

It was also verified, by Fourier transform infrared spectroscopy, that the treatment with hydrofluoric acid carried out during the third step makes it possible to remove the silica template. The appended FIG. 3 represents the FITR spectra obtained with the Msi silica template (FIG. 3a)), a silica matrix after impregnation with and crosslinking of a solution of phenol/formaldehyde resin: MSiScross (FIG. 3b)), a silica matrix of MSiScross type which has been subjected to a treatment with hydrofluoric acid but not to carbonization (FIG. 3c)), a crosslinked phenol/formaldehyde resin matrix obtained by simple crosslinking by heat treatment of 1 ml of Ablaphene® RS 101 phenol/formaldehyde resin in a glass sample tube (FIG. 3d)) and a carbon monolith MScarb (FIG. 3e)). In this FIG. 3, the transmittance expressed in arbitrary units is a function of the wavelength, expressed in $cm^{-1}$. The black arrow indicates the peak characteristic of SiO at 1076 cm$^{-1}$. The spectra 3a) and 3b) of the Msi and MSiScross monoliths both exhibit a strong absorption centered at 1076 cm$^{-1}$, signifying the presence of silica. In the spectrum 3d) corresponding to the pure phenol/formaldehyde resin matrix, this peak is of course absent, as is the case also in she spectra 3c) and 3e). These results demonstrate that the silica template was completely removed by the treatment with hydrofluoric acid. The spectrum of the MScarb carbon monolith is quite flat; the peaks corresponding to the Sp$^2$ and Sp$^3$ orbitals of the aromatic rings are located, respectively, at approximately 1650 cm$^{-1}$ and 1100 cm$^{-1}$.

The specific surface area measurements for each of the carbon monoliths obtained are collated in table 2 below:

TABLE 2

| Monoliths | MS25carb | MS60carb | MS80carb | MS80HF | MS90carb |
|---|---|---|---|---|---|
| Specific surface area by BET (m$^2 \cdot$g$^{-1}$) | 550 | 700 | 460 | 400 | 450 |
| Specific surface area by BJH (m$^2 \cdot$g$^{-1}$)$^a$ | — | 12 | 11 | 2 | 5 |
| Total pore volume (cm$^3 \cdot$g$^{-1}$) | 0.25 | 0.24 | 0.23 | 0.20 | 0.22 |

$^a$the BJH method was applied only to the pores having a diameter of greater than 17 Å and for the desorption curve It can be concluded from these results that the monoliths have a microporous nature (pore size between 7 and 12 Å), and do not exhibit mesoporosity.

Figure 4:
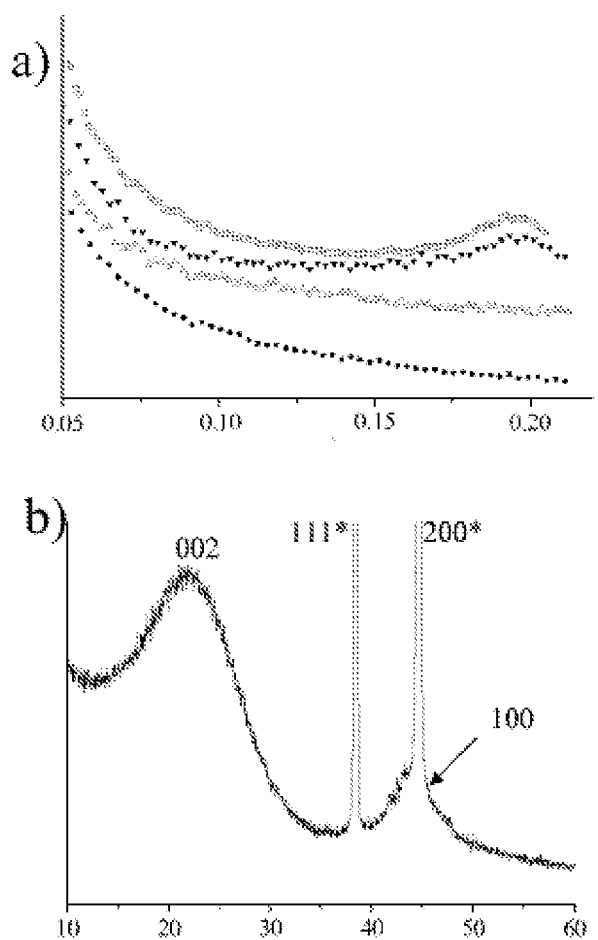
FIGS. 4a-4b are a porosity study and XRD diffraction spectrum for monoliths obtained in example 1, in accordance with one embodiment.

The study of the porosity on the mesoscopic scale evaluated by SAXS is given in the appended FIG. 4a). The scattering profiles were established for each of the carbon monoliths synthesized (MSi: □, MSiS80cross: ▼, MS80carb: Δ and MS80HF: ●). In this figure, the intensity, expressed in arbitrary units, is a function of the wave vector (q), expressed in Å$^{-1}$.

It is noted that the matrices formed of pure silica MSi and of silica impregnated with crosslinked resin MSiScross have an unordered mesoporosity with a distance between two pores of 32 Å (wave vector q=0.195 Å$^{-1}$). Moreover, an absence of mesoporosity is observed in the other monoliths.

When FIG. 4b), which represents the XRD diffraction spectrum of a carbon monolith of MS80HF type (intensity, in arbitrary units, as a function of the diffraction angle, in degrees), is considered, two main peaks (2Q=22° and 2Q=45°) are observed which correspond respectively to the peaks characteristic of the graphitized carbonaceous compounds (d(002)=0.4 nm and d(100)/d(101)).

The carbon monoliths of MScarb and MS80HF type thus graphitized exhibited a conductivity of about 10 S·cm$^{-1}$.

Figure 5:
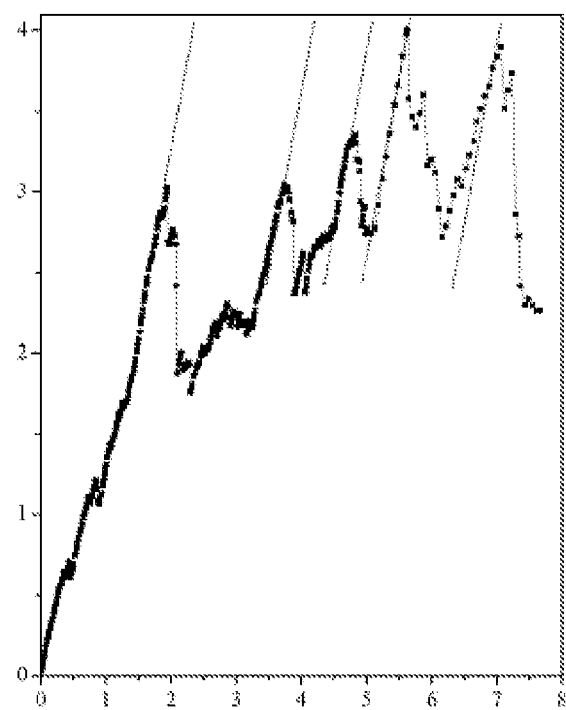
FIG. 5 shows the results of the mechanical compression tests carried out on carbon monoliths obtained in example 1, in accordance with one embodiment.

The results of the mechanical compression tests carried out on the carbon monolith MS80HF are given by the appended FIG. 5, in which the stress (in MPa) is a function of the strain (in %). The jagged curve reveals abrupt falls in the stress which are due to a partial rupture of the macroporous structure of the monolith (rupture of the wall of the macropores). In this figure, the oblique dotted lines demonstrate that each pinnacle begins with the same slope, whatever the value of the stress applied. This result signifies behavior under elastic conditions.

The mean Young's moduli calculated from these results are about 0.2 GPa and reflect the very high strength of the materials obtained, allowing them to be used for the manufacture of electrodes modified with electroactive entities for biosensors or biofuel cells.

Example 2

Preparation of an Enzymatic Sensor

In this example, an illustration is given of the preparation of an enzymatic sensor (ES) for detecting oxygen (O$_2$), starting from a carbon monolith and from bilirubin oxidase (BOD).

The carbon monolith used in this example was prepared exactly as described above in example 1, except that a 40% phenolic resin solution, i.e. a solution S40: Ablaphene® RS 110 at 40% by weight in THF, was used for the step of impregnation of the silica template as obtained in step 1) of example 1.

A silica monolith impregnated with the solution S40 was obtained, i.e. an MSiS40 monolith.

The carbon monolith was then synthesized according to the first synthesis route described above in step 3) of example 1.

A carbon monolith MS40carb was obtained, the porosity characteristics of which were as follows:
  Mesoporosity (nitrogen adsorption/desorption):
    Surface area of the micropores: 523 m$^2 \cdot$g$^{-1}$
    Micropore volume: 0.27 cm$^3 \cdot$g$^{-1}$
  Macroporosity (mercury porosymmetry):
    Intrusion volume: 1.73 cm$^3 \cdot$g$^{-1}$
    Porosity: 74%
    Bulk density: 0.43 g·cm$^3$
    Density of the skeleton: 1.64 g·cm$^3$ The carbon monolith MS40carb was then functionalized with the bioelectrocatalyst according to the following processes:

The carbon monolith was adhesively bonded to a glassy carbon electrode 5 mm in diameter (GC electrode, Pine, USA), by means of a conductive carbon paint, and was then subjected to a 1 Torr oxygen plasma for 15 minutes.

The electrode modified with the carbon monolith, was soaked in a solution of 1.7 mg/ml of BOD in a 20 mM phosphate buffer of pH 7.2, for one hour thirty minutes.

An enzymatic sensor BOD-MS40carb in accordance with the invention was thus obtained.

By way of comparative example No 1, a glassy carbon (GC) electrode 5 mm in diameter (Pine Research instrumentation, Raleigh, N.C., USA) was prepared and was impregnated with 5 μl of aqueous solution of BOD at 20 mg/ml.

An enzymatic sensor not in accordance with the invention, referred to as BOD-GC, was obtained.

By way of comparative example No. 2, another biosensor not in accordance with the invention was prepared starting from the MS40carb monolith, comprising bilirubin oxidase and a redox mediator, namely a copolymer of poly(N-vinylimidazole) and of poly(acrylamide) complexed with [Os (4,4'-dichloro-2,2'-bipyridine)$_2$Cl]$^{+/2+}$ (PAA-PVI-bipy). In this case, the bilirubin oxidase is not directly adsorbed to the internal surface of the macropores of the monolith, but attached to the surface of the macropores by means of the redox mediator. In this case, the MS40carb carbon monolith was impregnated with 66.6 μg of a mixture consisting of 51.6 μg of PAA-PVI-bipy, of 10.0 μg of POD and of 5.0 μg of PEGDGE (400).

An enzymatic sensor which is not part of the invention, referred to as BOD-Mediator-MS40carb, was thus obtained.

These three sensors were then tested for the detection of O$_2$ in a liquid medium. The measurements were carried out with a bipotentiostat (CH-Instrument, electrochemical detector, model CHI832) connected to a computer. The temperature of the liquid medium, made of a 20 mM phosphate buffer solution, was regulated at 37.5° C. using a thermostated bath (Fisher Scientific, Pittsburgh, Pa.).

The BOD-MS40carb, BOD-Mediator-MS40carb or BOD-GC enzymatic sensors were kept moving in the buffer using a Pine Instrument® agitator (Pine Research instrumentation, Raleigh, N.C., USA). The measurements were carried out in an electrochemical cell with a water bath.

The potentials were measured with a commercial Ag/AgCl (3 M KCl) reference electrode (BAS) and while using a platinum electrode (BAS) as counterelectrode.

Figure 6:
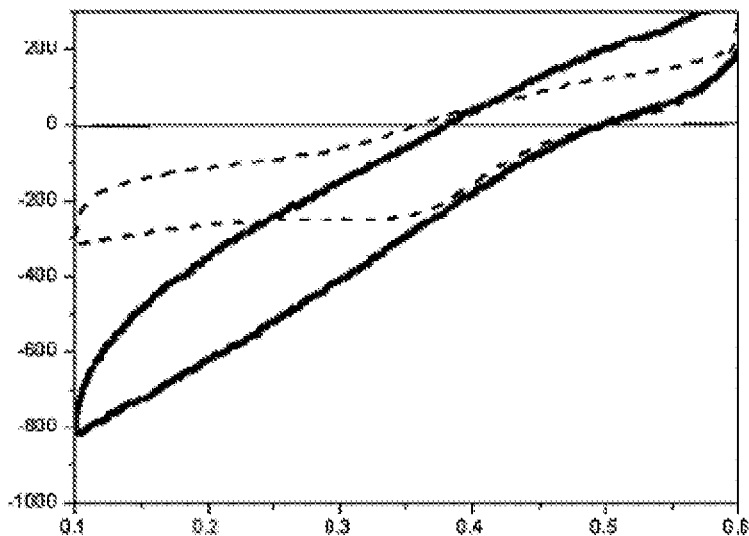
FIG. 6 shows the results obtained with the enzymatic sensors which show current density (in μA) as a function of the electric potential (in volts) on carbon monoliths obtained in example 2, in accordance with one embodiment.

The results obtained with the BOD-MS40carb, BOD-Mediator-MS40carb and BOD-GC enzymatic sensors are given in the appended FIG. 6, in which the current density (in μA) is a function of the electric potential (in volts).

In this figure, the curve as a continuous thick line represents the electroreduction of $O_2$ to $H_2O$ obtained with the BOD-MS40carb sensor in accordance with the invention, and the curve as a dashed line represents the electroreduction of $O_2$ to $H_2O$ obtained with the BOD-Mediator-MS40carb sensor which is not part of the invention and the curve as a continuous thin line corresponds to the recording made with the BOD-GC biosensor which is also not part of the invention. It is noted that the BOD-MS40carb sensor in accordance with the invention, i.e. in which the enzyme is in direct contact with the semi-graphitized graphite of the wall of the macropores, makes it possible to obtain better results than the BOD-Mediator-MS40carb sensor which is not part of the invention and in which the enzyme is attached to the wall of macropores by means of a redox mediator.

It is noted, moreover, that the current is negligible when the BOD-GC sensor is used.

Figure 7:
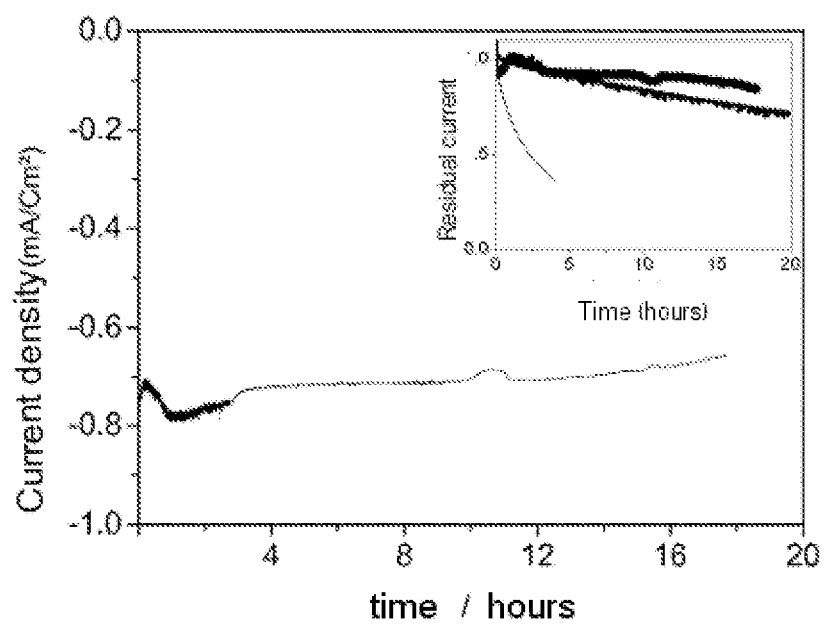
FIG. 7 shows test results for the change in the catalytic current density on carbon monoliths obtained in example 2, in accordance with one embodiment.

Finally, the change in the catalytic current density at 0 V of the BOD-MS40carb biosensor, in a 20 mM sodium phosphate buffer solution, pH 7.2, at a rotational speed of 1000 rpm, was tested and is given in the appended FIG. 7. In this figure, the current density (in $mA/cm^2$) is a function of time (in hours). It is observed that the catalytic current density for the BOD-MS40carb biosensor is stable as a function of time. By way of comparison, the inset figure in FIG. 7 shows the change in residual current for the BOD-MS40carb biosensor at 25° C. (very bold line) and at 37° C. (bold line), compared with the BOD-GC biosensor which is not part of the invention (thin line).

The invention claimed is:

1. A porous electrochemical electrode, comprising:
   a cellular solid material provided in the form of a semi-graphitized carbon monolith having a hierarchical porous network free of mesopores and having macropores with a mean dimension $d_A$ of from 1 μm to 100 μm, and micropores with a mean dimension $d_I$ of from 0.5 nm to 2 nm, said macropores and micropores being interconnected, and
   at least one electroactive entity selected from the group consisting of enzymes having a redox center, nucleic acids, antibodies, antigens and conductive polymers, and
   wherein the macropores contain said electroactive entity, said electroactive entity is in direct contact with the semi-graphitized carbon that makes up the surface of the macropores,
   said electrode does not have a redox mediator or an electrically conducting linker arm.

2. The electrode as claimed in claim 1, wherein the macropores of the semi-graphitized carbon monolith have walls having a thickness of from 0.5 μm to 40 μm.

3. The electrode as claimed in claim 1, wherein the macropores have a diameter of from 4 μm to 70 μm.

4. The electrode as claimed in claim 1, wherein the micropores have a diameter of from 0.7 nm to 1.5 nm.

5. The electrode as claimed in claim 1, wherein the semi-graphitized carbon monolith has a specific area being from 400 $m^2/g$ to 900 $m^2/g$.

6. The electrode as claimed in claim 1, wherein the electroactive entity is an enzyme having a redox center and is chosen from oxidoreductases.

7. The electrode as claimed in claim 6, wherein the macropores of the carbon monolith contain at least one cofactor chosen from oxidoreduction coenzymes and metal cations.

8. The electrode as claimed in claim 1, wherein the immobilized electroactive entity is present in an amount varying from 0.01% to 7% by weight relative to the total weight of the electrochemical electrode.

9. The electrode as claimed in claim 1, wherein the electroactive entity is immobilized within the macropores of the semi-graphitized carbon monolith of the electrochemical electrode by means of electrostatic interactions with the semi-graphitized carbon and also via steric constraints related to the size of the macropores.

* * * * *